(12) United States Patent
Mosler et al.

(10) Patent No.: US 6,767,370 B1
(45) Date of Patent: *Jul. 27, 2004

(54) FOOT INSERT FOR AN ARTIFICIAL FOOT

(75) Inventors: Lueder Mosler, Duderstadt (DE);
Martin Pusch, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/285,260

(22) Filed: Apr. 2, 1999

(30) Foreign Application Priority Data

Apr. 11, 1998 (EP) .............................. 98106689

(51) Int. Cl.[7] .................................. A61F 2/66
(52) U.S. Cl. ...................................... 623/55
(58) Field of Search ............... 623/55, 56, 53, 623/54; 36/27, 38

(56) References Cited

U.S. PATENT DOCUMENTS

| | | | | |
|---|---|---|---|---|
| 4,892,554 A | * | 1/1990 | Robinson | 623/55 |
| 4,959,073 A | | 9/1990 | Merlette | 623/55 |
| 5,139,525 A | | 8/1992 | Kirstinsson | 623/51 |
| 5,156,632 A | | 10/1992 | Wellershaus | 623/55 |
| 5,181,933 A | | 1/1993 | Phillips | 623/55 |
| 5,290,319 A | | 3/1994 | Phillips | 623/56 |
| 5,509,938 A | | 4/1996 | Phillips | 623/56 |
| 5,514,185 A | | 5/1996 | Phillips | 623/52 |
| 5,706,589 A | * | 1/1998 | Marc | 36/27 |
| 5,728,177 A | * | 3/1998 | Phillips | 623/55 |
| 5,800,570 A | * | 9/1998 | Collier | 623/55 |
| 5,897,594 A | * | 4/1999 | Martin et al. | 623/55 |
| 5,944,760 A | * | 8/1999 | Christensen | 623/55 |
| 6,007,582 A | * | 12/1999 | May | 623/55 |
| 6,029,374 A | * | 2/2000 | Herr et al. | 36/27 |
| 6,099,572 A | | 8/2000 | Mosler et al. | 623/53 |

FOREIGN PATENT DOCUMENTS

| | | |
|---|---|---|
| DE | 363 938 | 11/1922 |
| DE | 42 05 900 | 2/1992 |
| DE | 40 37 928 | 5/1992 |
| DE | 40 38 063 | 6/1992 |
| DE | 42 05 899 | 9/1992 |
| DE | 42 08 941 | 9/1993 |
| DE | 93 15 665.0 | 1/1994 |
| FR | 25 322 | 1/1923 |
| FR | 2 640 499 | 6/1990 |
| WO | 96/04869 | 2/1996 |

* cited by examiner

Primary Examiner—Bruce Snow
(74) Attorney, Agent, or Firm—Foley & Lardner LLP

(57) ABSTRACT

The invention relates to a resilient foot insert for an artificial foot, having at least one spring element that determines the spring rigidity of the artificial foot, and an adapting device for changing the spring rigidity of the spring element. In order to improve and simplify the adaptation of the foot insert to the respective use conditions, the invention provides that the adapting device be automatically actuated as a function of the respective loading to which the foot insert is subjected by the patient wearing the artificial foot.

28 Claims, 5 Drawing Sheets

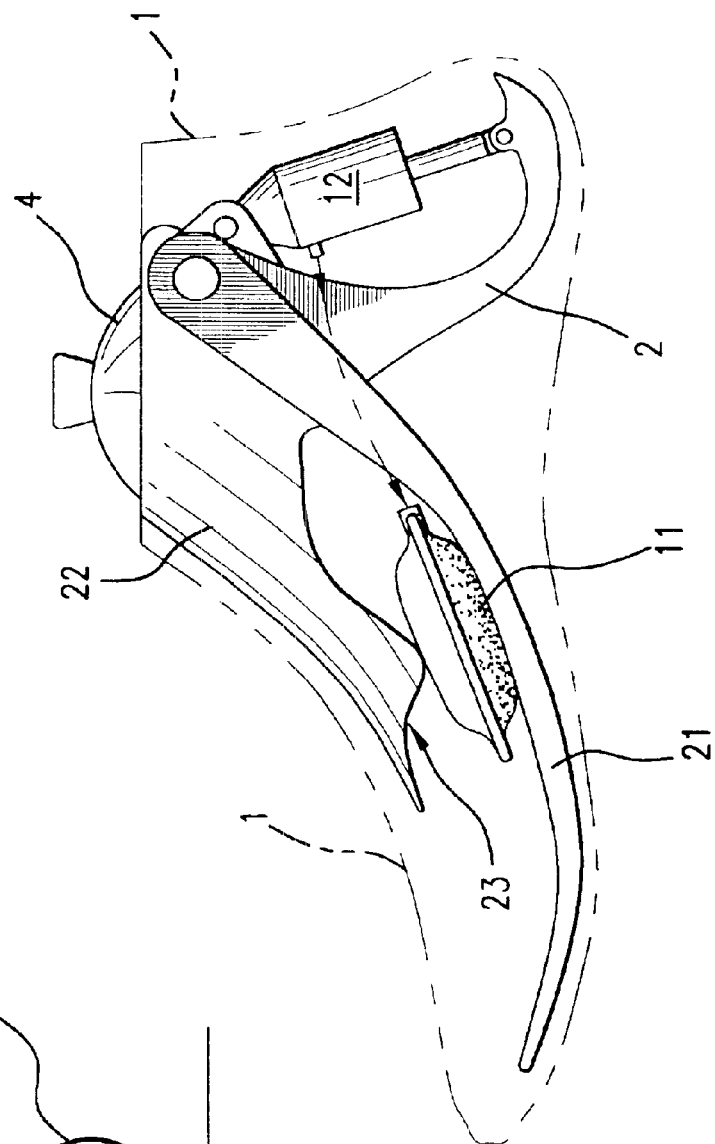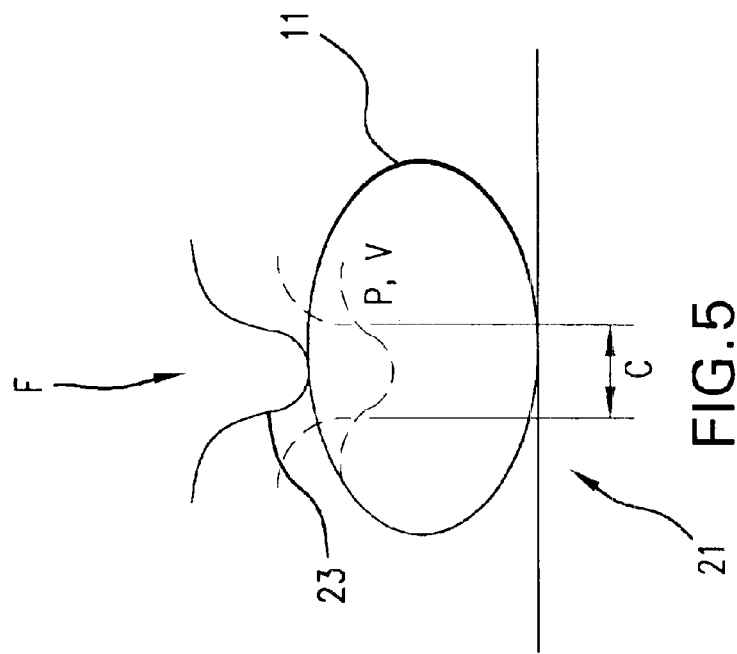

FOOT INSERT FOR AN ARTIFICIAL FOOT

BACKGROUND OF THE INVENTION

1. Field of the Invention

The invention relates to a novel resilient foot insert for an artificial foot, having at least one spring element for determining the spring rigidity of the artificial foot, and an adapting device for changing the spring rigidity of the spring element.

2. Description of Related Art

One embodiment of a foot insert described in DE-A 42 05 900 comprises three leaf springs. A leaf spring with shallow bends is arranged in the heel region and, by way of its front end, is connected to a bent forefoot spring in the forefoot region. One end of the bent forefoot spring extends upwardly into the foot-connection region and is screwed to an adapter. The other spring end projects into the front region of the foot. The forefoot spring is assigned a second, somewhat shorter leaf spring. The top end of the shorter leaf spring is screwed to the top end of the forefoot spring in the region of the adapter connection.

The area in which the shorter leaf spring joins the forefoot spring defines a receiving space which increases in size in a wedge-like manner toward the front. An air-filled pressure pad is supported by the forefoot spring and the shorter leaf spring in the receiving space. The patient can change the resiliency characteristics of this foot insert by changing the air pressure in the pressure pad. The pressure pad can be manually inflated with the aid of a hand pump. A valve device allows the interior pressure of the pressure pad to be reduced.

The walking dynamics of the patient are a function of the patient's form on a specific day and also of the activity which the patient is carrying out. It is quite conceivable for adaptation to the patient's form on a specific day to be carried out by a gradually adapting system (with the aid of an air-filled pad, as described above). On the other hand, adapting to a patient's activity at any one moment in time (e.g., at the workplace) may have to be done very quickly and, sometime, may need to be done from one step to the next. The presently known pneumatic systems are not quite capable of adapting as quickly as necessary.

The difficulties suggested in the preceding are not intended to be exhaustive, but are among many tending to reduce the effectiveness of the foot insert. Other noteworthy problems may exist; however, those presented above should be sufficient to demonstrate that such methods and apparatuses appearing in the past will admit to worthwhile improvements.

SUMMARY OF THE INVENTION

Accordingly, it is a general object of the invention to provide a foot insert for an artificial foot that will obviate or minimize the disadvantages of the type previously described.

It is a specific object of the invention to provide a foot insert for an artificial foot having increased wearing comfort.

It is another object of the invention to provide a foot insert for an artificial foot that adapts quickly to changes in the patient's activity.

A preferred embodiment of the invention, which is intended to accomplish at least some of the foregoing objects, includes at least one spring element for determining spring rigidity of the artificial foot; and an adapting device kinematically connected to the at least one spring element for changing a spring rigidity of the artificial foot, wherein the adapting device is actuated dependent on a load placed on the artificial foot.

Additional objects, features, and advantages of the invention will be set forth in the following description, and, in part, will be obvious from the description, or may be learned by practicing the invention. The objects and advantages of the invention may be realized and obtained by the instrumentalities and combinations particularly pointed out in the appended claims.

BRIEF DESCRIPTION OF THE DRAWINGS

The accompanying drawings, which are incorporated in and constitute part of the specification, illustrate presently preferred embodiments of the invention, and, together with the above general description and the following detailed description of the preferred embodiments, serve to explain the principles of the invention.

FIG. 4 is a modified embodiment of that shown in FIG. 1;

FIG. 5 is a schematic illustration of a detail from FIG. 4;

DETAILED DESCRIPTION OF THE PREFERRED EMBODIMENTS

Figure 1:
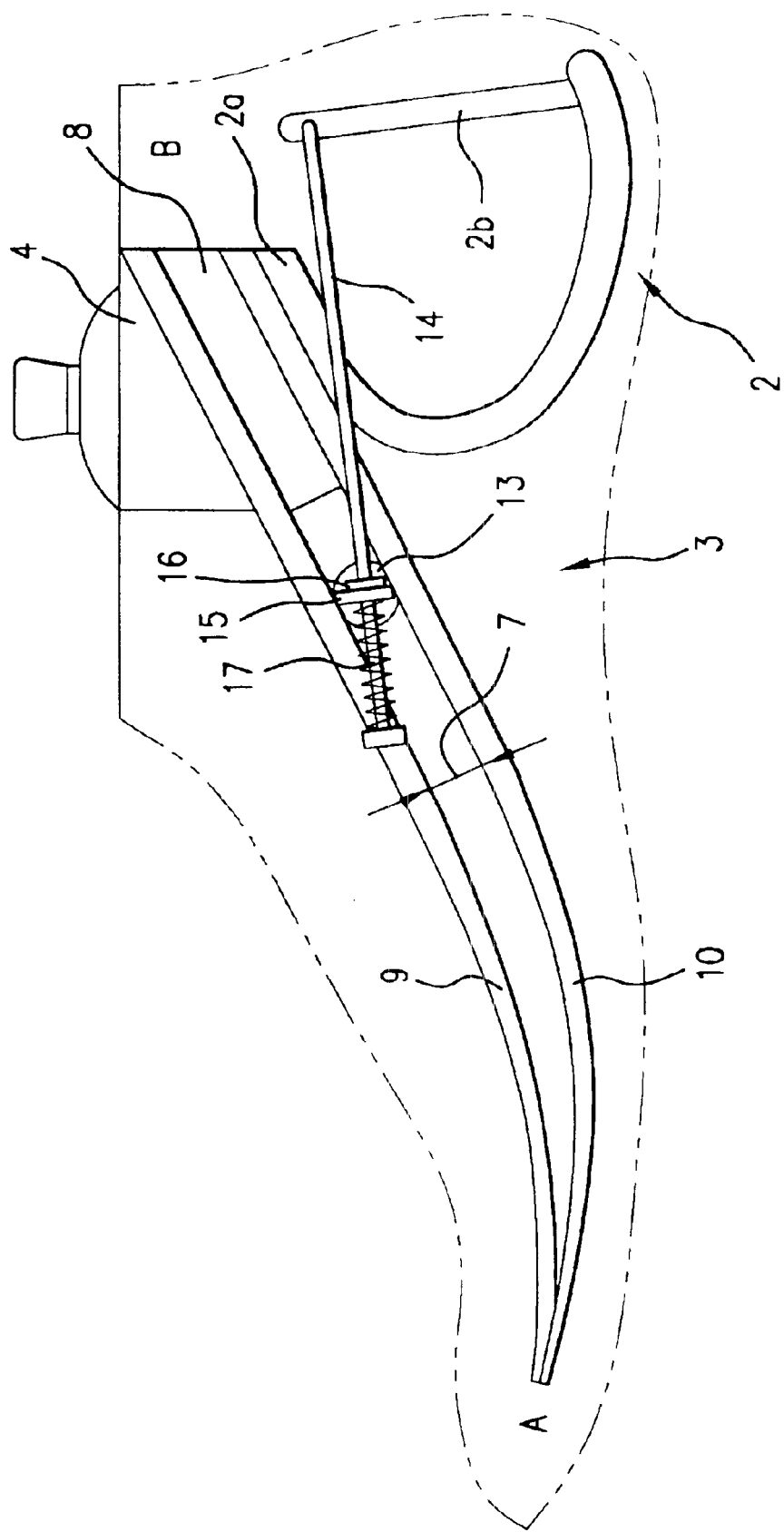
FIG. 1 is a side view of a mechanically self-adapting artificial foot with a spacer which is arranged in a longitudinally adjustable manner.

The adapting device according to the invention preferably is actuated dependent upon the respective loading to which the foot insert is subjected by the patient wearing the artificial foot.

In one preferred embodiment, it is preferable for the spring element to constitute a forefoot spring, and for the heel deflection in the foot insert, which is adjusted by the heel loading, to serve as the input variable for the automatic adjustment of the adapting device. As a result, the adjustment of the foot insert's rigidity is regulated as a function of the walking dynamics of the patient. Because the amount of spring movement of the heel is usually considerably smaller than that of the forefoot, the heel displacement has a lesser influence on the walking behavior. According to the invention, the heel deflection is thus used for controlling the forefoot rigidity.

In a further embodiment, it is advantageous for the adjustable spring element to constitute an air-filled pressure pad and for the adapting device to comprise an air pump that is driven by the heel deflection. In this embodiment, the air pressure in the pressure pad increases as the heel load is increased, and the air pressure in the pressure pad decreases as the heel load decreases. Preferably, the pressure pad has a positive-pressure valve that forms a constant positive-pressure leakage and is intended to reduce the air pressure in a predetermined time period.

In this case, as a result of the non-linear force/travel characteristics of a pneumatic spring, it is advantageous for the air-filled pressure pad to have a contoured abutment surface. The contoured abutment surface preferably projects onto the pressure pad and, upon penetrating the pressure pad, adapts to the progressing pressure increases due to the resulting decreased pressure pad volume, such that at least approximately linear force/travel characteristics of the pressure pad are obtained. Such linearization can also be achieved by a degressive advancement of the two abutment surfaces acting on the pressure pad therebetween.

In order to realize quick, automatic adaptation of the artificial foot to the walking dynamics of the patient at any one time, the invention provides that the adjustable spring element be a forefoot spring. The forefoot spring preferably is designed as a leaf spring that extends at least over the forefoot region. Preferably, the adapting device is a rigid spacer, which can be displaced in the longitudinal direction with respect to the forefoot spring. The adapting device preferably determines the spring rigidity of the forefoot spring and is displaced longitudinally by a mechanical adjusting device that is connected kinematically to the heel deflection. Upon maximum deflection, the mechanical adjusting device preferably causes maximum displacement of the spacer in the direction of the front end of the forefoot spring. The spacer returns to its original position when there is no longer any pressure on the forefoot.

In the case of this embodiment, if the patient takes a quick step and places his/her weight firmly onto the heel when the foot is placed on the ground, the spacer is displaced further forward. With the subsequent loading to which the forefoot is subjected, the position of the spacer is fixed. By means of the more rigid forefoot lever, the patient can then execute a longer step than would be possible with a more flexible forefoot lever.

After pressure is released from the forefoot, this fixing is terminated, and the spacer can return into its starting position. An arrangement of this type allows adaptation of the forefoot-spring rigidity for each individual step, which is advantageous for greatly varying activities.

Referring now to the figures, wherein like numerals represent like parts, and initially to FIG. 1, there will be seen a resilient foot insert having a heel spring 2, which is designed in the form of a C. The heel spring 2 is connected, via the top leg 2a of the C-spring 2, to the rear end region B of a forefoot spring 3. The top leg 2a of the C-spring 2 is screwed to an adapter 4. The adapter 4 allows the artificial foot to be connected to an artificial leg and thereby serves as an attachment member.

The forefoot spring 3, preferably, comprises two leaf-spring elements 9, 10, which are arranged in parallel alongside one another and are connected to one another to be rigid with respect to moments at their two end regions A, B. In this preferred embodiment, a spacing element 8 is provided between the two leaf-spring elements 9, 10 in the rear end region B. Between the two end regions A, B, the two leaf-spring elements 9, 10 are spaced apart by an unobstructed distance 7, in which there is a mechanical adapting element.

The bottom free leg end of the C-spring 2 is connected kinematically to a rigid spacer 13 via a push rod 14. That end of the push rod 14 that is oriented toward the front is guided in a longitudinally displaceable manner in a guide element 15. The guide element 15 is seated laterally on the spacer 13. The push rod 14 butts against the rear side of the guide element 15 via carrier plate 16 and is supported, via its free end, on the guide element 15 via a spring 17.

When taking a quick step, a patient places his/her weight firmly onto the heel as the foot is placed on the ground, and the C-spring 2 deforms (heel deflection), which then displaces the push rod 14. The push rod 14, via the carrier plate 16, pushes the spacer 13 forward. The spacer 13 is then fixed in place as the forefoot is subject to the subsequent loading. The spring 17 allows the heel spring to spring back without the position of the spacer 13 being changed as a result. After pressure no longer exists on the forefoot, the spacer 13 becomes free and returns into its starting position via the action of spring 17.

The preferred embodiment of FIG. 1 thus allows for a quick, automatic adapting of the artificial foot to the walking dynamics of the patient at any given time. The rigidity of the two-layered forefoot spring 3 is adjusted by the longitudinally displaceable mechanical spacer 13, which is controlled via the magnitude of the force with which the heel is placed on the ground.

Figure 2:
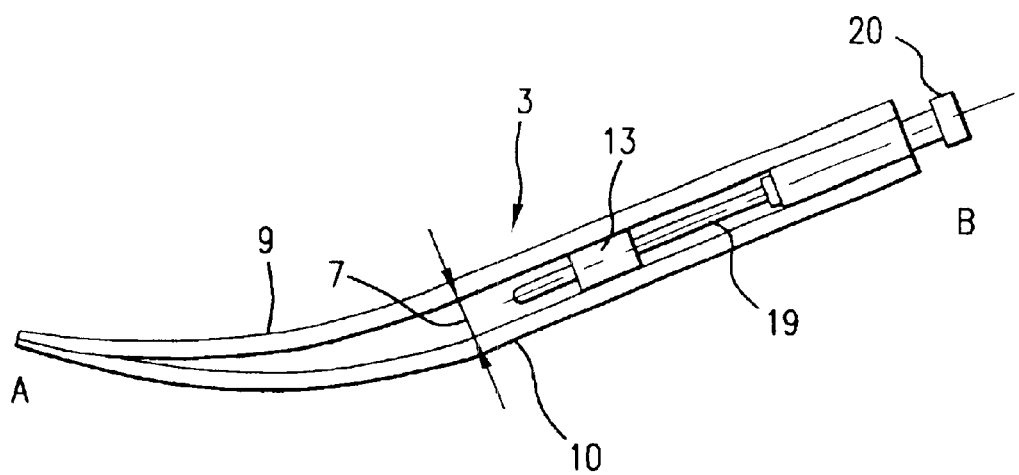
FIG. 2 is a detailed drawing of a modified embodiment of the device illustrated in FIG. 1.

Another preferred embodiment of the invention is shown in FIG. 2, in which there is a forefoot spring 3 comparable to that of FIG. 1. The rigid spacer 13, in this case, is displaced longitudinally along a spindle 19. The spacer 13 is guided therealong via a spindle nut (not illustrated specifically). The rear end 20 of the spindle 19 projects out of the rear end region B of the forefoot spring 3 and is connected there to a mechanical adjusting device (not illustrated specifically), which is connected kinematically to the heel deflection of the C-spring.

Figure 3:
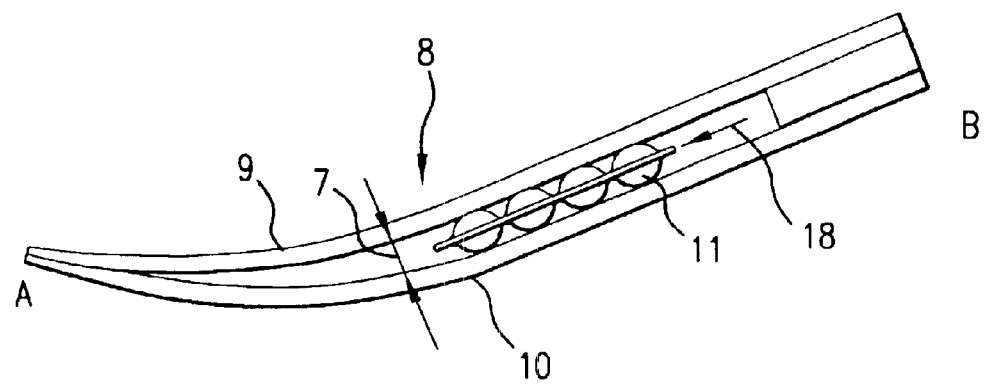
FIG. 3 shows, in longitudinal section in the sagittal plane, a forefoot spring with resilient pressure buffers.

Another embodiment of the invention is shown in FIG. 3, in which there is an elastic pressure pad 11 placed in the unobstructed distance 7 between the two leaf-spring elements 9, 10. As demonstrated by arrow 18, the elastic pressure pad 11 may be displaced in the longitudinal direction of the forefoot spring 3 by a mechanical device depending on the heel loading, e.g., by means of the aforementioned mechanical devices of the embodiments of FIGS. 1 and 2. In the alternative, the elastic pressure pad 11 may be inflated in the position illustrated, by means of a heel-loading-dependent control element.

The jointless artificial foot illustrated in FIG. 4 has a cosmetic covering 1 which is indicated by dotted lines and encloses a resilient foot insert in the form of an air-filled pressure pad 11. The pressure pad 11 rests on a pivotable base spring 21, which is likewise designed as a leaf spring. The pivotable base spring 21 extends into the forefoot and its rear end articulates pivotably in the top region of the C-spring 2. A leg 22 of the foot insert, which is preferably of rigid design, acts on the top side of the pressure pad 11. The abutment surface 23 of the rigid leg 22 is contoured.

The air-filled pressure pad 11 is connected to the pressure connection stub of an air-pump element 12, which is arranged in the space enclosed by the C-spring 2. The air-pump element preferably is actuated dependent upon the patient's weight and/or the activity being carried out by the patient. The C-spring 2 is compressed somewhat under heel loading. The change in distance between the two C-spring legs 2a, 2b, which defines a heel deflection, preferably constitutes the drive for the air-pump element 12.

As shown in FIG. 5, the leg 22 has a leg abutment surface 23 with a surface C that corresponds to a surface of the pressure pad 11. Upon the leg abutment surface 23 penetrating the pressure pad 11, the surface C adapts to the progressing pressure increases resulting from the decrease in volume in the pressure pad 11, such that at least approximately linear force/travel characteristics of the pressure pad 11 are obtained. In this case, the surface C is projected in the force direction F depicted.

Since pneumatic springs usually have non-linear force/travel characteristics, the abutment surface 23 is contoured, according to the invention, so as to produce linearized characteristic lines. In the isothermal case, the force/travel behavior of such air-filled pressure pads is a function of the abutting surface C projected in the force direction and of the reciprocal value of the residual volume V in the pressure pad, with the interior pressure P of the latter then being obtained from the quotient F/C.

Figure 6:
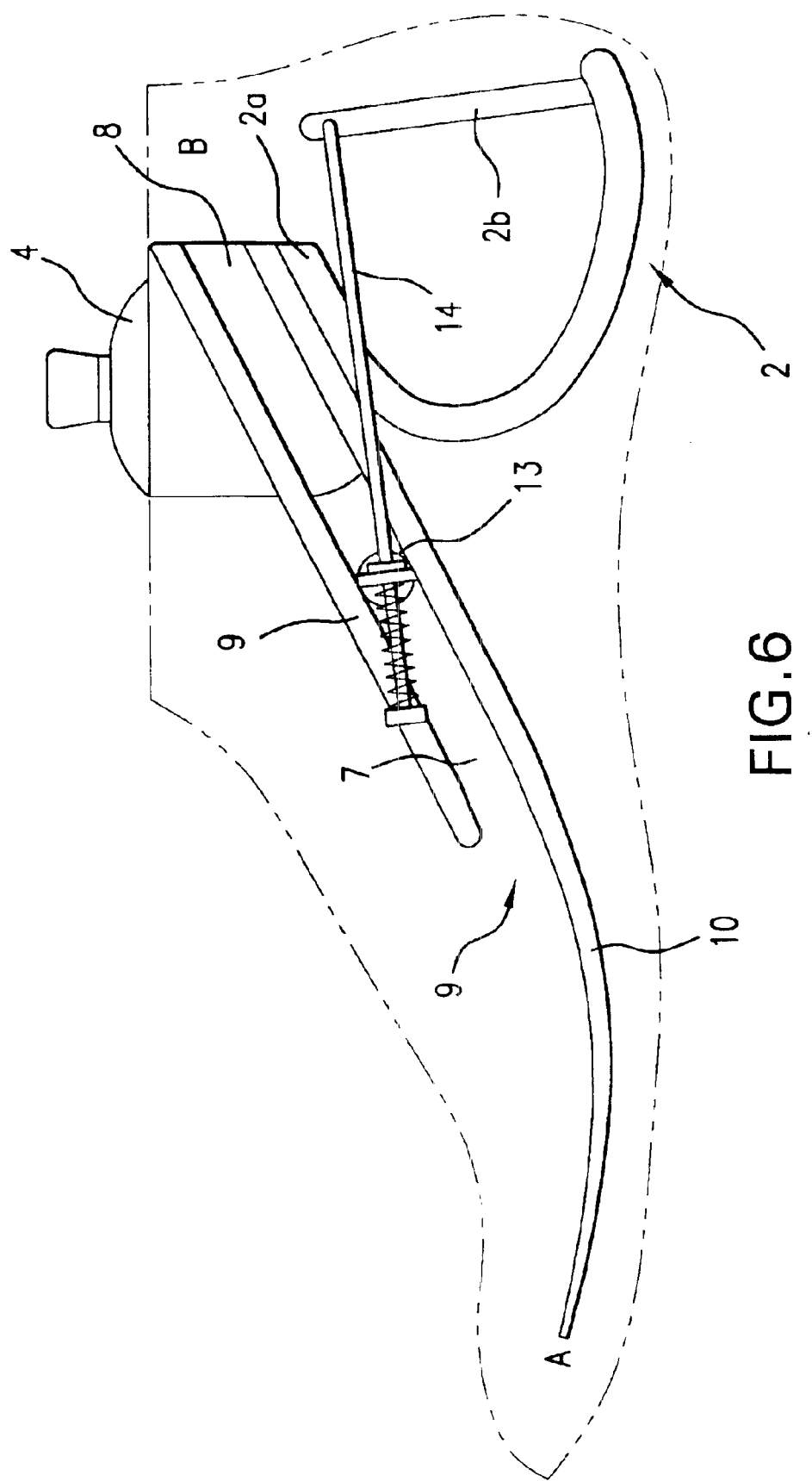
FIG. 6 is a modified embodiment of that shown in FIG. 1.

The embodiment according to FIG. 6 is similar to the embodiment shown in FIG. 1 in terms of the spacer 13 and the kinematic connection of the spacer 13 to the C-spring 2. In this embodiment, however, the two leaf-spring elements 9, 10, which form the forefoot spring 3, are coupled to one another only at their rear end B in a manner so as to be rigid with respect to moments.

Figure 7:
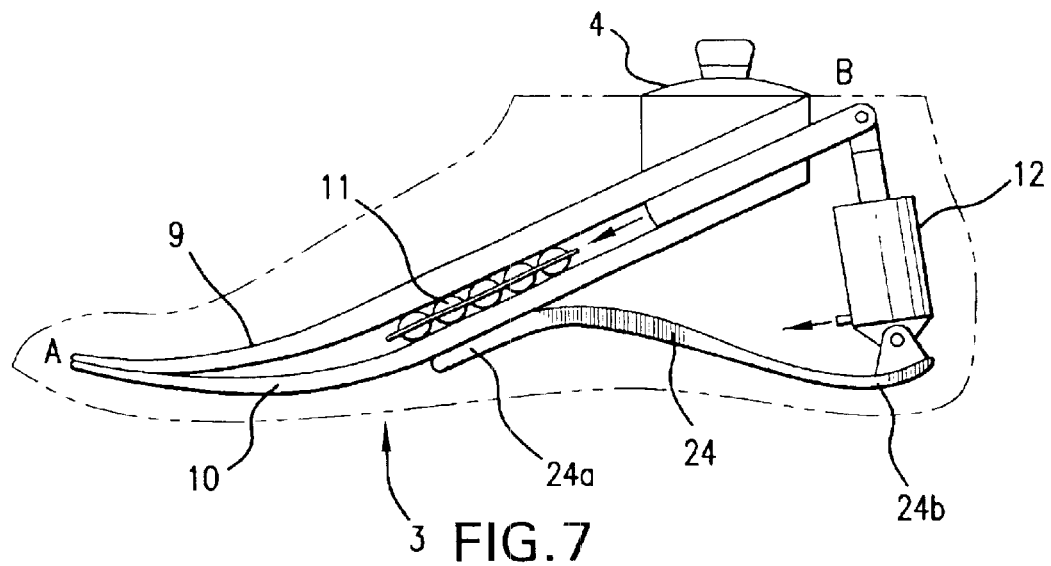
FIG. 7 is a modified embodiment of that shown in FIG. 1.

Another preferred embodiment of the foot insert is illustrated in FIG. 7. This embodiment has a forefoot spring 3 that extends over virtually the entire length of the foot insert, and a heel spring 24 that is designed in the form of a shallow sine wave. At approximately the central longitudinal region of the forefoot spring 3, the heel spring 24 is fastened to the underside of the forefoot spring 3 via its front leg end 24a. The adapting device, once again, is an air-pump element 12 that is arranged between the rear leg end 24b of the heel spring 24 and the rear end of the forefoot spring 3. Here, once again, a pneumatically adapting design is employed having an advantage that greater bending of the forefoot ensures greater overall displacement of the adapting device. When an air pump is used as the adapting device, it is the case that more air is taken in and more air is delivered into the air-filled pressure, pads 11 and, thus, into the forefoot. With successful adaptation, the bending of the forefoot decreases as a result of the greater spring rigidity, with the result that the pump again delivers its normal volume of air.

Figure 8:
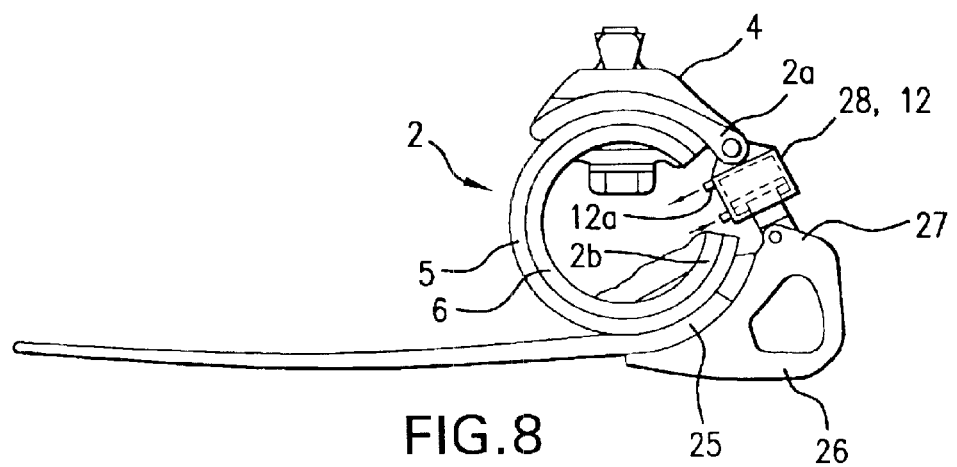
FIG. 8 is a further-modified embodiment of that illustrated in FIG. 1.

Yet another embodiment is shown in FIG. 8, which comprises a base spring 21 extending over virtually the entire length of the foot insert, and a C-spring 2 that is arranged in the heel region. The foot insert absorbs the prosthesis loading via the top C-leg 2a of the C-spring 2. The bottom C-leg 2b rests on a rearwardly extended saddle 25 formed by the rear end of the base spring 21. The saddle 25 is supported on a heel wedge 26. Provided between the top C-leg 2a and a bearing block 27, which is arranged behind said leg, is a tie in the form of a pneumatic cylinder 28 (not illustrated specifically) which has a progressive force/travel characteristic line. Moreover, an air pump 12 is located between the top C-leg 2a and the bearing block 27. The pressure-connection stub 12a of the air pump 12 is connected to the pneumatic cylinder 28.

The pneumatic cylinder 28 thus serves as a tie element for changing the resilient properties of the spring insert. By way of the moment resulting from it, forefoot loading leads to widening of the C-spring 2. The forces which occur here are to be transferred into the base fastening via the tie element. However, the tie element is intended to, act in both directions of the deformation of the C-spring, that is, when the spring bends closed and when it bends open. In this case, the bending-closed action of the C-spring is to be as smooth as possible initially, while, with further deformation, the inhibiting effect which the tie element has on the deformation of the C-spring is to increase. For the patient, this progression constitutes an easier rolling action onto the forefoot, because the C-spring, which is assisted by a tie of this type, may be configured to be more flexible.

In this case, the forefoot resistance, which is perceptibly lower for the patient, is also reflected in a progressive ankle moment during the stance phase of a step. For this progression to be actively controlled automatically dependent upon the respective loading to which the foot insert is subjected by the patient wearing the artificial foot, the adapting means provided is an air pump 12, which is arranged in parallel with the pneumatic cylinder and is connected to the pneumatic cylinder 28 by way of its pressure connection stub. The pneumatic cylinder 28 is not seen in FIG. 8, because it is located behind the air pump 12. Sometimes, it is preferable for the cross-section of the air pump 12 to be smaller than the cross-section of the pneumatic cylinder 28. If the air pump 12 forces an additional quantity of air into the pneumatic cylinder 28, the basic pressure of the pneumatic cylinder 28 and, thus, the rigidity of that pneumatic cylinder 28, are increased. The pressure in the pneumatic cylinder may be reduced, again, via a leakage.

The rear tie mounting, which is provided on the bearing block 27, is preferably located in the Achilles' tendon region. The front or top tie mounting may act directly on the adapter 4.

In summary, in the embodiment of FIG. 8, the tie element controls the inhibition of the bending-open action of the C-spring 2 dependent upon the previous bending-closed action of the C-spring 2, which corresponds to the heel loading. Since the forefoot rigidity is determined by the arrangement of the C-spring 2 and base spring 21 in series, the result is a progressive characteristic line which is controlled by the progressive displacement inhibition of the tie element. In this case, the advantage of this embodiment is that influencing the tie element characteristics can influence the forefoot rigidity as well as the characteristic line thereof. A smoother, progressive characteristic line facilitates the rolling action of the foot, but allows only restricted walking dynamics and energy recovery. A less smooth, linear characteristic line, in contrast, allows higher walking dynamics, but is uncomfortable at low walking speeds.

Additional advantages and modifications will readily occur to those skilled in the art. Therefore, the invention in its broadest aspects is not limited to the specific details, and representative devices, shown and described herein. Accordingly, various modifications may be made without departing from the spirit or scope of the general inventive concept as defined by the appended claims and their equivalents.

Priority document, European Patent Application No. 98106689.7, filed Apr. 11, 1998, is hereby incorporated by reference.

What is claimed is:

1. An artificial foot, comprising:
    a covering defining an artificial foot having a forefoot region and a heel region; and
    a resilient foot insert placed inside of said covering and comprising:
        a first spring element comprising at least one forefoot leaf spring element extending into the forefoot region of the foot insert for determining spring rigidity of the artificial foot;
        a second spring element located at least in part in the heel region of the artificial foot;
        an attachment member connected to at least one of said spring elements, for mounting the artificial foot to a prosthesis; and
        an adapting device actuated in response to flexing of said second spring element and operatively connected to the second spring element for changing the spring rigidity of the artificial foot by changing the spring rigidity of the forefoot leaf spring element responsive to a load placed on the artificial foot which causes flexing of the second spring element, wherein the adapting device is operatively connected to the forefoot leaf spring element for directly changing its bending resistance and wherein deflection of the second spring element in the heel due to flexing thereof comprises an input variable for actuating the adapting device.

2. An artificial foot as claimed in claim 1, wherein said second spring member comprises a C-spring in the heel region having a top end, a bottom end and a leg extending from the top end;

said forefoot spring member comprises a pivotable base spring pivotably connected to the C-spring and extending into the forefoot region; and the adapting device comprises a pressure pad mounted to the pivotable base spring; and a pump element mounted between the top and bottom ends of the C-spring and in fluid communication with the pressure pad, wherein the pump element increases the volume of the pressure pad as a load increases in the heel region.

3. An artificial foot as claimed in claim 2, wherein the pressure pad includes a pressure valve for reducing a pressure therein within a predetermined period of time.

4. An artificial foot as claimed in claim 1, wherein said forefoot spring member comprises two leaf springs;

said second spring member comprises a C-spring having a top end and a bottom end, said C-spring being mounted in the heel region and being connected to one of the two leaf springs; and said adapting device comprises an element mounted between the two leaf springs for adjusting the rigidity of the leaf springs and being responsive to displacement of the C-spring.

5. An artificial foot as claimed in claim 4, wherein the adapting element comprises a spacer.

6. An artificial foot as claimed in claim 5, wherein the adapting device further comprises a push rod mounted to the C-spring and mechanically connected to the spacer.

7. An artificial foot as claimed in claim 5, wherein the adapting device further comprises a guide element for guiding the push rod in the spacer.

8. An artificial foot as claimed in claim 5, wherein the adapting device further comprises a spring mounted on the push rod between the spacer and an end of the push rod in the forefoot region.

9. An artificial foot as claimed in claim 4, further comprising a spacing element mounted between the two leaf springs in the heel region for producing a spacing distance between the two leaf springs from the heel region until a front end of the forefoot region.

10. An artificial foot as claimed in claim 4, further comprising an adapter mounted to said C-spring, wherein the adapter is adapted for mounting to a prosthesis.

11. An artificial foot as claimed in claim 4, wherein the adapting element comprises a spindle between the two leaf springs and a rigid spacer mounted on the spindle.

12. An artificial foot as claimed in claim 4, wherein the adapting element comprises an elastic pressure pad, and the elastic pressure pad is mechanically coupled to the C-spring.

13. An artificial foot as claimed in claim 12, wherein the adapting device further comprises a pump mounted between the top and bottom ends of the C-spring and fluidly communicating with the elastic pressure pad.

14. An artificial foot as claimed in claim 4, wherein both leaf springs extend over approximately an entire length of the foot insert.

15. An artificial foot as claimed in claim 4, wherein only one of the two leaf springs extends over an entire length of the foot insert.

16. An artificial foot as claimed in claim 1, wherein the first spring element comprises a forefoot spring having a front end and a rear end and extending approximately the entire length of the foot insert, and the second spring element comprises a heel spring fastened at its front end to an underside of the forefoot spring and with its rear end extending into the heal region, wherein the heel spring is formed as a shallow sine wave, and wherein the adapting device is arranged between the rear end of the heel spring and the rear end of the forefoot spring.

17. An artificial foot as claimed in claim 16, wherein a front end of the heel spring is fastened at approximately the center of the underside of the forefoot spring.

18. An artificial foot as claimed in claim 1, wherein the first spring element comprises a forefoot spring having a front end and a rear end and extending approximately the entire length of the foot insert, and the second spring element comprises a heel spring with its rear end extending into the heel region.

19. An artificial foot as claimed in claim 1, wherein said attachment member transfers load placed on the artificial foot to cause flexing of the second spring element.

20. An artificial foot as claimed in claim 1, wherein said attachment member is connected to both of said first and second spring elements.

21. An artificial foot as claimed in claim 1, wherein said adapting device changes the bending resistance of said forefoot leaf spring so that said change continues during forefoot loading of the artificial foot.

22. An artificial foot as claimed in claim 1, wherein said forefoot leaf spring extends at least over said forefoot region.

23. An artificial foot, comprising:

a covering defining an artificial foot having a forefoot region and a heel region; and a resilient foot insert placed inside of said covering and comprising:

at least one first spring element for determining spring rigidity of the artificial foot;

a second spring element located at least in part in the heel region of the artificial foot;

an attachment member connected to at least one of said spring elements, for mounting the artificial foot to a prosthesis; and an adapting device operatively connected to the at least one first spring element for changing a spring rigidity of the artificial foot, wherein the at least one first spring element includes a forefoot spring comprising a leaf spring, wherein deflection of said second spring element in the heel comprises an input variable for controlling the adapting device, wherein the adapting device is actuated dependent on a load placed on the artificial foot, and wherein the adapting device comprises a pressure pad mounted on the at least one first spring element, and a pump fluidly communicating with the pressure pad for increasing and decreasing the volume of the pressure pad responsive to the load on the heel to change the bending resistance of said leaf spring.

24. An artificial foot as claimed in claim 23, wherein the pressure pad includes a pressure valve for reducing a pressure therein within a predetermined period of time.

25. An artificial foot as claimed in claim 23, wherein the at least one spring element includes a contoured abutment surface projecting onto a surface of the pressure pad.

26. An artificial foot as claimed in claim 25, wherein the contoured abutment surface adapts to a pressure increase in the pressure pad to achieve an approximately linear force characteristic for the pressure pad.

27. An artificial foot, comprising:
   a covering defining an artificial foot having a forefoot region and a heel region; and
   a resilient foot insert placed inside of said covering and comprising:
      a first spring element comprising at least one forefoot leaf spring element extending into the forefoot region of the foot for determining spring rigidity of the artificial foot;
      a second spring element located at least in part in the heel region of the artificial foot;
      an attachment member connected to at least one of said spring elements, for mounting the artificial foot to a prosthesis; and
      means, operatively connected to the second spring element, for changing the spring rigidity of the artificial foot by directly changing the bending resistance of the forefoot spring element responsive to flexing of said second spring element due to a load placed on the artificial foot, wherein deflection of the second spring element in the heel due to flexing thereof comprises an input variable for actuating the means for changing the spring rigidity of the artificial foot.

28. An artificial foot as claimed in claim 27, wherein said changing means comprises means for changing the bending resistance of said forefoot leaf spring so that said change continues during forefoot loading of the artificial foot.

* * * * *